United States Patent [19]

Berendes et al.

[11] 4,277,459
[45] Jul. 7, 1981

[54] PROCESS FOR WORKING UP ORGANIC REACTION MIXTURES

[75] Inventors: Otto Berendes, Dormagen, Fed. Rep. of Germany; Karl-Heinz Vopel, Leawood, Kans.

[73] Assignee: Bayer Aktiengesellschaft, Leverkusen, Fed. Rep. of Germany

[21] Appl. No.: 121,210

[22] Filed: Feb. 13, 1980

Related U.S. Application Data

[63] Continuation of Ser. No. 3,432, Jan. 12, 1979, which is a continuation of Ser. No. 883,758, Mar. 6, 1977, abandoned, which is a continuation of Ser. No. 785,276, Apr. 6, 1977.

[30] Foreign Application Priority Data

Apr. 23, 1976 [DE] Fed. Rep. of Germany ....... 2617812

[51] Int. Cl.$^3$ .......................................... C01B 17/033
[52] U.S. Cl. ............................. 423/567 A; 423/578 R; 71/49
[58] Field of Search .............. 423/567, 578; 23/308 S; 260/986, 990; 21/4

[56] References Cited

U.S. PATENT DOCUMENTS

| 3,089,890 | 5/1963 | Chupp et al. | 260/990 |
|---|---|---|---|
| 3,304,158 | 3/1968 | Dale | 423/578 |
| 3,502,750 | 3/1970 | Anglaret et al. | 260/990 X |

FOREIGN PATENT DOCUMENTS

346835  4/1931  United Kingdom ..................... 423/578

*Primary Examiner*—G. O. Peters
*Attorney, Agent, or Firm*—Sprung, Felfe, Horn, Lynch & Kramer

[57] ABSTRACT

Organic reaction mixtures, particularly of mixtures containing contaminant organic phosphorus compounds and/or sulfur, are worked up by introducing the mixture into water which has been made alkaline and has a temperature of from $-10°$ to $+50°$ C., a pH value of at least 10 being maintained in the resulting mixture, separating the aqueous phase from the sulfur which separates out; and contacting the aqueous phase or the sulfur which has separated out with nitric acid at an elevated temperature and a pH of below 3.

5 Claims, No Drawings

PROCESS FOR WORKING UP ORGANIC REACTION MIXTURES

This is a continuation of Ser. No. 003,432 filed Jan. 12, 1979, which in turn was a continuation of Ser. No. 883,758 filed Mar. 6, 1977 now abandoned, which in turn was a continuation application of patent Ser. No. 785,276 filed Apr. 6, 1977.

This invention relates to the working up of organic reaction mixtures, particularly of mixtures containing contaminant organic phosphorus compounds and/or sulfur.

A mixture of dialkyldithiophosphoryl chloride and sulfur is obtained by chlorinating dialkylthiophosphoric acid by known processes (for example U.S. Pat. No. 3,089,890). The mixture can be worked up by distilling off the dialkylthiophosphoryl chloride. The distillation residue which results is sulfur, together with unstable, evil-smelling by-products which contain organic phosphorus compounds.

If the distillation residue, which contains sulfur and unstable, evil-smelling by-products which contain organic phosphorus compounds, is passed into water which has been rendered alkaline, the phosphorus-containing, hydrolyzable compounds are largely dissolved in the alkaline water. The sulfur, however, is chiefly produced in a plastic, contaminated form in which it can scarecely be used again and must therefore be conveyed to a controlled tip. In addition, the effluent which is formed has a high chemical oxygen demand and cannot be passed to the main outfall in this form. Although a treatment with known oxidizing agents such as $H_2O_2$, peroxy disulpate or sodium hypochlorite is possible, it is expensive, produces no by-products which can be utilized and as a rule further increases the salt burden.

In the present invention residues from the above-mentioned or similar reactions, in which evil-smelling by-products which contain organic phosphorus compounds, and/or sulfur are simultaneously produces, are worked up while isolating valuable by-products.

it has now been found that both the effluent which is formed when the distillation residue is introduced into water which has been rendered alkaline, and also the resulting plastic sulfur, which is strongly contaminated, can be converted into valuable fertilizers and virtually pure crystalline sulfur, respectively.

The process of the present invention is one for working up residues containing organic phosphorus compounds and/or containing at least partially plastic, contaminated sulfur, (e.g., such as are formed as a distillation residue in particular in the production of dialkylthiophosphoric acid chlorides by chlorinating the dialkyldithiophosphoric acids formed from phosphorus pentasulphide and the corresponding alcohols) comprising introduction of the residue into the water which has been rendered alkaline and has a temperature of from −10° to +50° C., a pH value of at least 10 being maintained in the resulting mixture, separating off the aqueous phase from the sulfur which has separated out and bringing the aqueous phase and/or the sulfur which has separated out into contact with nitric acid at elevated temperature, at pH values below 3, preferably at pH values of <1. The treatment with nitric acid can be used to convert the material into a fertilizer and/or crystalline sulfur.

Alternative methods of performing the process according to the invention are described below, particularly in connection with working up a distillation residue, such as is formed in the removal by distillation of dialkylthiophosphoryl chloride in accordance with U.S. Pat. No. 3,089,890.

The hot distillation residue from the production of thiophosphoric acid ester-chloride is quenched, while cooling and preferably while stirring, in water which has been rendered alkaline. The water should have been rendered sufficiently alkaline to give always a pH value of at least 10, preferably of 11. The water taken, which has been rendered alkaline preferably has an OH concentration of 0.5 to 2 mols/l. Examples of suitable alkali compounds are alkali metal hydroxides and alkali metal carbonates. Potassium hydroxide and/or potassium carbonate are preferably employed. When the hot distillation residue is chilled, the sulphur is produced in a form which is to some extent tacky and plastic. The resulting mixture contains only relatively little chloride from the hydrolyzable residue from the production of phosphoric acid ester-chloride.

The liquid phase in the resulting mixture is now separated off, for example via decantation, from the sulphur which is settling out.

There are various embodiments for the treatment, according to the invention, of the liquid phase an/or the sulphur with nitric acid.

If it is merely intended to purify the contaminated, partly plastic sulphur and to convert it into crystalline sulphur, the sulphur is then heated at elevated temperature, preferably 90° to 105°, with about 10 to 40% strength nitric acid until an evolution of nitric oxide subsides and until a well crystallized form is obtained.

If it is merely intended to work up the liquid phase which contains the compounds containing organic phosphorus, this liquid phase is brought into contact at temperatures of 80° to 110° C., preferably 90° to 105° C., with 60% strength to 100% strength, preferably 64 to 98% strength nitric acid, in such a way that there is always a pH value of <3, preferably <1, in the resulting mixture. In the course thereof, the nitric acid is reduced to nitric oxides by the oxidizable impurities in the effluent. At the end of the nitric acid treatment, the resulting liquid phase is neutralized, preferably by means of ammonia or potassium hydroxide or potassium carbonate. A nearly odorless liquid with an only slightly yellowish color which can contain valuable fertilizer salts, such as ammonium nitrate, potassium nitrate, diammonium hydrogen phosphate and ammonium sulphate, is obtained in this way. By adding further inorganic or organic plant nutrients, for example urea, as well as trace elements, it is possible, depending on end use, to prepare a specific fertilizer which can be produced either as a highly concentrated liquid fertilizer or, after spray drying, as fertilizer granules.

In the preferred embodiment of the process according to the invention, the liquid phase containing the compounds which contain organic phosphorus compounds, such as is obtained after quenching in the aqueous alkaline medium and separation of the sulphur, is treated with nitric acid, but in the presence of the sulphur. A liquid containing fertilizer salts and nearly pure, crystalline sulphur, which can easily be separated from one another, are produced simultaneously in this embodiment. This embodiment is described in a general form in the following text: the hot distillation residue from the production of thiophosphoric acid ester-chloride is quenched, for example in excess aqueous potassium hydroxide solution, while cooling and stirring. In the course thereof, as already described, the sulphur is produced in a form which is to some extent tacky and plastic. In the resulting mixture, the liquid phase which contains organic phosphorus compounds is separated off from the sulfur which is settling out. The moist sulphur is then armed to about 60° to 100° C., preferably 70° to 90° C. while stirring. The liquid phase which has been separated off and nitric acid of a concentration of 64 to 98% are then added simultaneously to the sulphur residue, specifically in such a ratio that the pH value in the mixture of sulphur and resulting liquid phase which now forms, is always below 3, preferably below 1. The temperature of the resulting mixture is adjusted in such a way that the mixture preferably boils under reflux. Nitric oxide is evolved and the sulphur changes its form and becomes visibly more crystalline, although the temperature rises. The color of the effluent becomes lighter. After the addition of the two liquid phases to the sulphur taken is complete, the mixture is allowed to boil under reflux for about a further 30 to 180 minutes. The nitric oxide which is still present in the mixture can be removed, for example by passing air through the mixture, but it can also be reduced to nitrogen by adding a little urea. Before the subsequent separation, for example filtration, of the now crystalline sulphur, it is advantageous to neutralize the batch with ammonia (in the form of gas or as a concentrated solution), while cooling.

It is advisable to carry out the oxidation in the continuous form described, since if highly concentrated nitric acid is introduced into the aqueous alkaline phase containing a compound which contains organic phosphorus, the evolution of nitric oxide is at first retarded but then begins in a very sudden and violent manner. It is also possible to employ mixtures of nitrates, such as sodium nitrate or potassium nitrate, and strong acids, such as sulphuric acid or phosphoric acid, instead of nitric acid in the process according to the invention, that is to say to cause the nitric acid to be formed in situ.

The nitrogen monoxide which is predominantly formed in the nitric acid treatment can be removed from the exit air by various known methods. Firstly, it is possible, for example, to absorb the nitrogen monoxide as nitrite and nitrate in multi-stage washers charged wit alkali, by feeding in air. There is also the possibility of converting the nitric oxide into nitric acid again, analogously to the Ostwald process. Depending on the size of an industrial plant, it is sometimes advisable to omit a recovery of nitric acid and instead to reduce the nitric oxides, for example by means of hydrogen or natural gas, to nitrogen, which can be released into the atmosphere without danger.

The process according to the invention therefore makes it possible to recover sulphur in a high-grade form, while simultaneously obtaining valuable fertilizers. The process according to the invention also causes no pollution of effluents and requires no expensive oxidising agents.

In the following text the process according to the invention is illustrated by means of examples:

EXAMPLE 1

Approximately 200 g, corresponding to the distillation residue of a 4 mol batch of dimethylthiophosphoryl chloride, prepared analogously to U.S. Pat. No. 3,089,980 were introduced at a temperature of 90° to 100° C. and while stirring vigorously, into a mixture of 70 g of 50% strength potassium hydroxide solution and 400 ml of ice water in a 1 l flask, equipped with stirrer, reflux condenser, thermometer and 2 dropping funnels. After 15 minutes the stirrer was stopped, and the sulphur was allowed to settle out. The aqueous alkaline phase was transferred into one of the dropping funnels. The other dropping funnel was filled with 100 to 200 ml of 98% strength nitric acid (2.4 to 4.8 mols). The sulphur residue was then heated to 70° to 90° C. with the aid of an oil bath and the aqueous alkaline phase and the nitric acid were added dropwise, at the same rate, to the nearly molten sulphur. The pH value in the resulting mixture was kept below <1. The temperature was raised slowly so that the batch boiled steadily under gentle reflux. A steady stream of nitric oxide was evolved. The time for the dropwise addition of the aqueous separated phase and the nitric acid was 40 to 60 minutes. The mixture was then boiled under reflux for a further one to two hours. In the course of the treatment the sulphur became light yellow and well crystalline, and the reflux temperature gradually rose to 102° to 105° C. during the reaction. After completion of the oxidation, the residual nitric oxides were blown out with air (time required approximately 10 minutes). The batch was cooled to 30° to 40° C. and was neutralized by passing in ammonia gas (approximately 70 to 100 g were consumed). The sulphur was then separated off by filtration and was rinsed with a little distilled water. Yield of pure sulphur: 80 to 110 g (62–85% of theory). After appropriate dillution, the filtrate could be used direct, for example as a fertilizer for grass.

EXAMPLE 2

Approximately 90–95 g of a distillation residue from a 2 mol batch of diethylthiophosphoryl chloride (prepared in accordance with Example 1) were worked up as described in Example 1. The aqueous alkaline phase was separated off from the sulphur and was treated separately. 100 ml of water were added to the sulphur and the mixture was heated to 70°–90° C. with the aid of an oil bath. 15–25 ml of 98% strength nitric acid or 25–40 ml of 65% strength nitric acid (0.36 to 0.6 mol) were added dropwise within approximately 20–30 minutes to the sulphur at this temperature. A rise in temperature to 99° C. was observed and a steady current of nitric oxide was evolved. The mixture was subsequently boiled for a further one to two hours. During this time the sulphur became light yellow and crystalline. After the oxidation the residual nitric oxides were expelled with air (time required approximately 10 minutes) and the residue of nitrite was destroyed by means of approximately 1–5 g of urea. The batch was cooled to 30°–40° C. and neutralized with dilute sodium hydroxide solution. The sulphur was then filtered off and well washed with distilled water. The yield was 50–57 g (78–89% of theory).

EXAMPLE 3

Approximately 150 g of a distillation residue at a temperature of 90° to 100° C., from a 3 mol batch of dimethylthiophosphoryl chloride (prepared in accordance with Example 1) were quenched, as described in Example 1, in a mixture of approximately 60 g of 50% strength potassium hydroxide solution and 300 ml of ice water in a flask equipped with stirrer, reflux condenser, thermometer and three dropping funnels. After approximately 15 minutes, the stirring was interrupted and the sulphur settled out. The aqueous alkaline phase was transferred into one of the three dropping funnels, the second dropping funnel was filled with approximately 250 g of concentrated sulphuric acid and the third dropping funnel was filled with a concentrated aqueous sodium nitrate solution (305 g of sodium nitrate is equivalent to 3.6 mols, and 340 ml of water.) The sulphur residue was heated to 70° to 90° C. and the previously separated aqueous alkaline phase, the sulphuric acid and the sodium nitrate solution were added dropwise uniformly within approximately 60 minutes. The pH value of the solution was always kept below pH 1 with the aid of the sulphuric acid. (Consumption of concentrated sulphuric acid approximately 250 g). Nitric oxide was evolved and the temperature rose to 106° to 108° C. The mixture was then boiled under reflux for 2 to 3 hours. The sulphur became well crystalline and light yellow. After the oxidation the residual nitric oxides were blown out with air and the residual nitrite was destroyed by means of approximately 1 to 5 g of urea. The batch was cooled to 30° to 40° C. and neutralized with ammonia gas (consumption approximately 90 g). The sulphur was then filtered off and washed with water. The yield of pure sulphur was approximately 75 g=78% of theory. After appropriate dilution, the filtrate could be used direct, for example as a fertilizer for grass.

It will be understood that the specification and examples are illustrative but not limitative of the present invention and that other embodiments within the spirit and scope of the invention will suggest themselves to those skilled in the art.

What is claimed is:

1. Process for working up an organic reaction mixture residue containing sulfur and organic phosphorus compounds, comprising the steps:
    (a) mixing the residue with alkaline water and maintaining the mixture at a pH of at least 10 to form an alkaline liquid phase comprising water and organic phosphates, and a solid phase comprising sulfur;
    (b) separating the alkaline liquid phase from the solid phase;
    (c) heating the solid phase to about 60°–100° C. while stirring;
    (d) Mixing the solid phase with the alkaline liquid phase and sufficient nitric acid to form an acidic reaction mixture with the pH maintained below 3;
    (e) heating the acidic reaction mixture to form, simultaneously, purified crystalline sulfur and a liquid suitable as a fertilizer; and
    (f) separating the purified crystalline sulfur from the liquid.
2. Process as claimed in claim 1 wherein the nitric acid is in a concentration of from about 3 to about 40 percent and the acidic reaction mixture is heated to a temperature of about 90° C. or above.
3. Process as claimed in claim 1 wherein the nitric acid is at a concentration of from about 60 to about 100 percent and the acidic reaction mixture is heated to a temperature of from about 80° to about 110° C.
4. Process as claimed in claim 1 wherein the acidic reaction mixture is at a pH of about 1.
5. Process as claimed in claim 1 wherein said reaction mixture residue is a distillation residue formed in the production of a dialkylthiophosphoric acid chloride by chlorination or the corresponding dialkyldithiophosphoric acid produced from phosphorus pentasulphide and the corresponding alkanol.

* * * * *

UNITED STATES PATENT AND TRADEMARK OFFICE
CERTIFICATE OF CORRECTION

PATENT NO. : 4,277,459
DATED : Jul. 7, 1981
INVENTOR(S) : Otto Berendes et al

It is certified that error appears in the above-identified patent and that said Letters Patent are hereby corrected as shown below:

Column 6, line 21    Delete "3" and insert --10--.

Signed and Sealed this

Sixteenth Day of February 1982

[SEAL]

Attest:

GERALD J. MOSSINGHOFF

Attesting Officer    Commissioner of Patents and Trademarks